(12) United States Patent
Ma et al.

(10) Patent No.: US 10,345,236 B1
(45) Date of Patent: Jul. 9, 2019

(54) METHOD FOR INSPECTING THE WATER CONTENT AND OXYGEN TRANSMISSIBILITY OF AN OPHTHALMIC LENS AND OPTICAL INSPECTING SYSTEM FOR INSPECTING AN OPHTHALMIC LENS

(71) Applicant: National Applied Research Laboratories, Taipei (TW)

(72) Inventors: Chia-Lien Ma, Hsinchu (TW); Hsin-Yi Tsai, Hsinchu (TW); Chih-Ning Hsu, Hsinchu (TW); Yu-Hsuan Lin, Hsinchu (TW); Kuo-Cheng Huang, Hsinchu (TW); Joi-Tsang Shum, Hsinchu (TW)

(73) Assignee: NATIONAL APPLIED RESEARCH LABORATORIES, Taipei (TW)

( * ) Notice: Subject to any disclaimer, the term of this patent is extended or adjusted under 35 U.S.C. 154(b) by 0 days.

(21) Appl. No.: 16/033,279

(22) Filed: Jul. 12, 2018

(30) Foreign Application Priority Data

May 23, 2018 (TW) .............................. 107117625 A

(51) Int. Cl.
| | | |
|---|---|---|
| *G01B 9/00* | (2006.01) | |
| *G01N 21/59* | (2006.01) | |
| *G01N 15/08* | (2006.01) | |
| *G02C 7/04* | (2006.01) | |
| *G01N 21/17* | (2006.01) | |

(52) U.S. Cl.
CPC ............. *G01N 21/59* (2013.01); *G01N 15/08* (2013.01); *G02C 7/049* (2013.01); *G01N 2015/0846* (2013.01); *G01N 2021/1748* (2013.01)

(58) Field of Classification Search
CPC ............. G01M 11/31; G01M 11/0207; G01M 11/0285; G01M 11/08; A45C 11/005; G02C 7/04; G02C 7/022; G02C 7/085; G02B 26/023; G02B 1/043; C08F 283/12; C08F 283/124
USPC .................................. 356/124–137; 523/107
See application file for complete search history.

(56) References Cited

U.S. PATENT DOCUMENTS

| | | | |
|---|---|---|---|
| 8,937,111 B2 * | 1/2015 | Alli ........................ | G02B 1/043 523/107 |
| 9,612,365 B2 * | 4/2017 | Alli ........................ | G02B 1/043 |
| 10,180,374 B1 * | 1/2019 | Lin .................... | G01M 11/0228 |

OTHER PUBLICATIONS

Tsai, et al., Fast photoelectric estimation of oxygen transmissibility of silicone hydrogel contact lens, Proceedings of the 6th International Conference on Photonics, Optics and Laser Technology, 2018, pp. 205-212, vol. 1, Science and Technology Publications, Lda.

* cited by examiner

*Primary Examiner* — Hoa Q Pham
(74) *Attorney, Agent, or Firm* — Haynes and Boone LLP

(57) ABSTRACT

The present invention provides a method for inspecting the water content and oxygen transmissibility of an ophthalmic lens and an optical inspecting system for inspecting an ophthalmic lens. Through the voltage variation from the measurement of transmitted light the water content and oxygen transmissibility of an ophthalmic lens are obtained. The oxygen transmissibility of the ophthalmic lens which is not under the specific condition specified by the standardized inspecting method can also be obtained.

20 Claims, 4 Drawing Sheets

METHOD FOR INSPECTING THE WATER CONTENT AND OXYGEN TRANSMISSIBILITY OF AN OPHTHALMIC LENS AND OPTICAL INSPECTING SYSTEM FOR INSPECTING AN OPHTHALMIC LENS

CROSS-REFERENCE TO RELATED APPLICATION AND CLAIM OF PRIORITY

The application claims the benefit of Taiwan Patent Application No. 107117625, filed on May 23, 2018, at the Taiwan Intellectual Property Office, the disclosures of which are incorporated herein in their entirety by reference.

FIELD OF THE INVENTION

The invention is related to a method and system for inspecting the water content and oxygen transmissibility, and more particularly to a method for inspecting the water content and oxygen transmissibility of an ophthalmic lens and an optical inspecting system for inspecting an ophthalmic lens.

BACKGROUND OF THE INVENTION

An ophthalmic lens can be any ophthalmic device that resides in or on the eye. These devices can provide optical correction or cosmetic enhancement. For example, an ophthalmic lens can be a contact lens, intraocular lens, overlay lens, ocular insert, optical insert or other similar device. Take the contact lens for example. Currently the contact lens inspecting method used in testing or manufacturing firms is mostly the coulometric method or the polarographic method. Although the two methods are certified by the International Organization for Standardization (ISO), the two methods cause relative inconvenience for measurement due to time-consuming operation, hard-to-carry equipment and being easily affected by the environment.

Related prior patents are mainly about contact measurements. There was not much innovation in the measurement methods of water content and oxygen transmissibility (Dk/t, where Dk is oxygen permeability and t is the thickness of the ophthalmic lens). Although the measurement methods are well-developed, those contact measurement methods based on electrochemical theory would cause doubts in health and safety and occurrence of user discomfort. Therefore, novel non-contact inspection technology and small measurement modules are desirable.

In order to overcome the drawbacks in the prior art, a method for inspecting the water content and oxygen transmissibility of an ophthalmic lens and an optical inspecting system for inspecting an ophthalmic lens are disclosed.

SUMMARY OF THE INVENTION

The present invention can effectively solve the above-mentioned problems in the prior art. The present invention provides a non-contact inspection method and a small optical inspecting system to quickly, conveniently, hygienically and safely obtain information of the water content and oxygen transmissibility of an ophthalmic lens, for doctors and manufacturers to evaluate the suitability and performance of the ophthalmic lens. Thus, the present invention has utility in the industry and significant practical applications.

In accordance with one aspect of the present invention, a method for inspecting a water content of a test ophthalmic lens is disclosed. The method includes: (a) emitting an incident light having an irradiation path and a first light intensity; (b) converting the first light intensity into a first voltage; (c) placing the test ophthalmic lens in the irradiation path; (d) emitting the incident light to pass through the test ophthalmic lens to obtain a transmitted light having a second light intensity at a $T_0$ instant; (e) converting the second light intensity into a second voltage; (f) calculating a difference between the first voltage and the second voltage to obtain an initial attenuation voltage; and (g) obtaining the water content of the test ophthalmic lens based on the initial attenuation voltage.

In accordance with a further aspect of the present invention, a method for inspecting an oxygen transmissibility of a test ophthalmic lens is disclosed. The method includes: (a) emitting an incident light having an irradiation path and a first light intensity; (b) converting the first light intensity into a first voltage; (c) placing the test ophthalmic lens in the irradiation path; (d) emitting the incident light to pass through the test ophthalmic lens to obtain a transmitted light having a second light intensity $I_{2(0)}$ at a $T_0$ instant; (e) repetitively measuring at time points from $T_1$ to $T_n$ the transmitted light with a time interval of $\Delta t$ to obtain a plurality of subsequent second light intensities $I_{2(\Delta t)}$, $I_{2(2\Delta t)}$, ... and $I_{2(n\Delta t)}$, where n is a positive integer; (f) converting the second light intensity and the plurality of subsequent second light intensities into a plurality of second voltages $V_{2(0)}$, $V_{2(\Delta t)}$, $V_{2(2\Delta t)}$, ... and $V_{2(n\Delta t)}$; (g) obtaining a difference of the first voltage and each of the plurality of second voltages to obtain a plurality of attenuation voltages; (h) identifying a highest value in the plurality of attenuation voltages, wherein the highest value occurs at a specific time point $T_s$ being one selected from the group consisting of $T_0$, $T_1$ to $T_n$; (i) finding from the plurality of attenuation voltages a specific attenuation voltage after a preset specific time period less than 7 minutes from $T_s$; (j) calculating a difference of the specific attenuation voltage and the highest value to obtain a difference voltage; and (k) introducing the difference voltage into an oxygen transmissibility-voltage relationship established by a plurality of standardized ophthalmic lenses to obtain the oxygen transmissibility of the test ophthalmic lens.

In accordance with another aspect of the present invention, a method for inspecting an oxygen transmissibility of a test ophthalmic lens is disclosed. The method includes: (a) placing the test ophthalmic lens in an irradiation path of an incident light; (b) emitting the incident light to pass through the test ophthalmic lens to obtain a transmitted light having a light intensity $I_0$ at a $T_0$ instant; (c) repetitively measuring the transmitted light at time points from $T_1$ to $T_n$ with a time interval of $\Delta t$ to obtain a plurality of subsequent light intensities $I_{\Delta t}$, $I_{2\Delta t}$, ... and $I_{n\Delta t}$, where n is a positive integer; (d) converting the light intensity and the plurality of subsequent light intensities into a plurality of voltages $V_0$, $V_{\Delta t}$, $V_{2\Delta t}$, ... and $V_{n\Delta t}$; (e) identifying a highest value in the plurality of voltages, wherein the highest value occurs at a specific time point $T_s$ being one selected from the group consisting of $T_0$, $T_1$ to $T_n$; (f) finding from the plurality of voltages a specific voltage after a preset specific time period less than 7 minutes from $T_s$; (g) calculating a difference of the specific voltage and the highest value to obtain a difference voltage; and (h) obtaining the oxygen transmissibility of the test ophthalmic lens based on the difference voltage.

In accordance with another aspect of the present invention, a method for inspecting an oxygen transmissibility of a test ophthalmic lens, wherein the test ophthalmic lens is made of a specific material, a standardized ophthalmic lens made of the specific material has a standardized initial attenuation voltage, and the standardized ophthalmic lens under a specific condition has a standardized oxygen transmissibility, is disclosed. The method includes: (a) emitting an incident light having an irradiation path, wherein the incident light has a first light intensity; (b) placing the test ophthalmic lens in the irradiation path; (c) passing the incident light through the test ophthalmic lens to generate a transmitted light having a second light intensity at a $T_0$ instant; (d) converting the first and the second light intensities into a first and a second voltages respectively, wherein the difference between the first and the second voltages is an initial attenuation voltage; (e) dividing the initial attenuation voltage by the standardized initial attenuation voltage to obtain a constant of proportionality; and (f) multiplying the standardized oxygen transmissibility by the constant of proportionality to obtain the oxygen transmissibility of the test ophthalmic lens.

In accordance with another aspect of the present invention, an optical inspecting system for inspecting an ophthalmic lens is disclosed. The optical inspecting system includes: a light source emitting an incident light having an irradiation path; a photo detector inspecting a first light intensity of the incident light and inspecting a second light intensity of a transmitted light obtained when the incident light passes through the ophthalmic lens at an instant being one selected from a group consisting of $T_0, T_1 \ldots T_{n-1}$ and $T_n$ where n is a positive integer; a signal amplifier circuit converting the first and the second light intensities into a first and a second voltages respectively; and a computer processing unit calculating a water content and an oxygen transmissibility of the ophthalmic lens according to the first and the second voltages, wherein the water content is measured at the $T_0$ instant.

BRIEF DESCRIPTION OF THE DRAWINGS

The details and advantages of the present invention will become more readily apparent to those ordinarily skilled in the art after reviewing the following detailed descriptions and accompanying drawings.

DETAILED DESCRIPTION OF THE PREFERRED EMBODIMENT

The present invention will now be described more specifically with reference to the following embodiments. It is to be noted that the following descriptions of the preferred embodiments of this invention are presented herein for the purposes of illustration and description only; they are not intended to be exhaustive or to be limited to the precise form disclosed.

Figure 1:
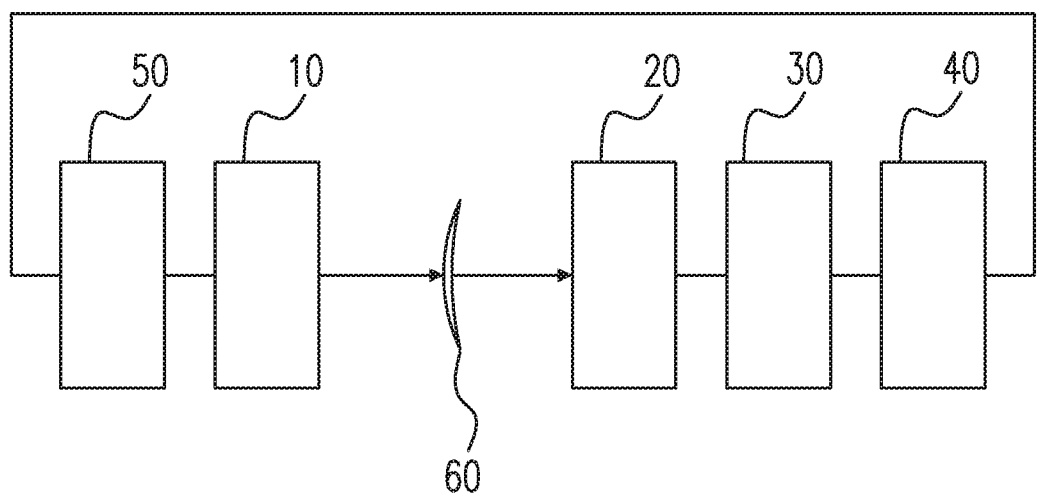
FIG. 1 is a schematic diagram of an optical inspecting system according to an embodiment of the present invention.

Please refer to FIG. 1, which is a schematic diagram of an optical inspecting system 100 according to an embodiment of the present invention. A light source 10 emits an incident light having an irradiation path. In FIG. 1, the arrow starting from the light source 10 represents the irradiation path of an embodiment of the present invention. An ophthalmic lens 60 can be placed in the irradiation path. In an example, the incident light is a monochromatic light. In an example, the light source 10 is a green light-emitting diode (LED). In an example, the green light-emitting diode emits a green light having a 520 nm wavelength and is triggered by a 1 mA current. In an embodiment, the optical inspecting system 100 further comprises a holding unit (not shown in FIG. 1) for holding the ophthalmic lens 60. The incident light passes through the ophthalmic lens 60 to generate a transmitted light. A photo detector 20 detects the light intensities of the incident light and the transmitted light. A signal amplifier circuit 30 electrically connected to the photo detector 20 converts the light intensities into voltages. In an embodiment, an aperture diaphragm (not shown in FIG. 1) is configured between the holding unit and the photo detector 20 for controlling the amount of light entering the photo detector 20. In an example, the signal amplifier circuit 30 is so designed that the voltage decreases as the light intensity increases. A computer processing unit 40 electrically connected to the signal amplifier circuit 30 calculates the water content and oxygen transmissibility of the ophthalmic lens according to the voltages. In an embodiment, a voltage measurement unit (not shown in FIG. 1) may be configured between the signal amplifier circuit 30 and the computer processing unit 40 for measuring values of the voltages and then sending the values of the voltages to the computer processing unit 40 for calculation. In an example, the voltage measurement unit is an oscilloscope. In an embodiment, a controller 50 is electrically connected to the computer processing unit 40 and the light source 10. The controller 50 adjusts the light intensity of the incident light emitted from the light source 10.

The ophthalmic lenses from different manufacturers may all be made of materials of a specific type. In an embodiment, the materials of the specific type are silicone hydrogels. In an embodiment for which the materials of the specific type are silicone hydrogels, the ophthalmic lenses are all contact lenses. Materials of a specific type can include plural specific materials. For example, a silicone hydrogel contact lens may be made of Senofilcon A, Narafilcon A, Filcon I or Somofilcon A. The package of contact lenses sold in stores usually indicates the water content measured by a standardized inspecting method, and information related to the oxygen transmissibility, like the oxygen transmissibility Dk/t or the oxygen permeability Dk, under a specific condition (usually being a power of −3.00 D). If it is the oxygen permeability that is indicated, then the oxygen transmissibility can be calculated through inspecting the thickness t of the ophthalmic lens. The ophthalmic lens having a water content measured by a standardized inspecting method and information related to the oxygen transmissibility under a specific condition is called a standardized ophthalmic lens in the present specification. The water content of the standardized ophthalmic lens is called a standardized water content, and the oxygen transmissibility of the standardized ophthalmic lens under a specific condition is called a standardized oxygen transmissibility. The water content of an ophthalmic lens is determined by its material. For example, silicone hydrogel contact lenses made of different specific materials may have different water contents. But the oxygen transmissibility of a contact lens is also related its diopter. When being inspected, a contact lens leaves the soaking solution. Initially the water content changes with time and affects the light intensity of transmitted light. Then the oxygen transmissibility starts to affect the light intensity of transmitted light. The above characteristics allow a method that can quickly, conveniently, hygienically and safely obtain the water content and oxygen transmissibility equivalent to those inspected by standardized inspecting method and the optical inspecting system thereof to be devised by the present invention.

Please refer to FIG. 1 again. The method using the optical inspection system 100 to inspect the water content of a test ophthalmic lens 60 includes: (a) emitting incident light having a first light intensity from the light source 10 to the photo detector 20 so that the first light intensity is measured; (b) converting the first light intensity into a first voltage with the signal amplifier circuit 30; (c) placing the test ophthalmic lens 60 in the irradiation path; (d) emitting the incident light from the light source 10 to pass through the test ophthalmic lens 60 to obtain transmitted light having a second light intensity at a $T_0$ instant and measuring the second light intensity at the $T_0$ instant with the photo detector 20; (e) converting the second light intensity into a second voltage with the signal amplifier circuit 30; (f) calculating a difference between the first voltage and the second voltage to obtain an initial attenuation voltage; and (g) obtaining the water content of the test ophthalmic lens 60 based on the initial attenuation voltage. In an embodiment, calculating a difference between the first voltage and the second voltage means subtracting the first voltage from the second voltage. In an embodiment, the initial attenuation voltage is introduced into a water content-voltage relationship established by a plurality of standardized ophthalmic lenses to obtain the water content of the test ophthalmic lens 60.

Figure 2:
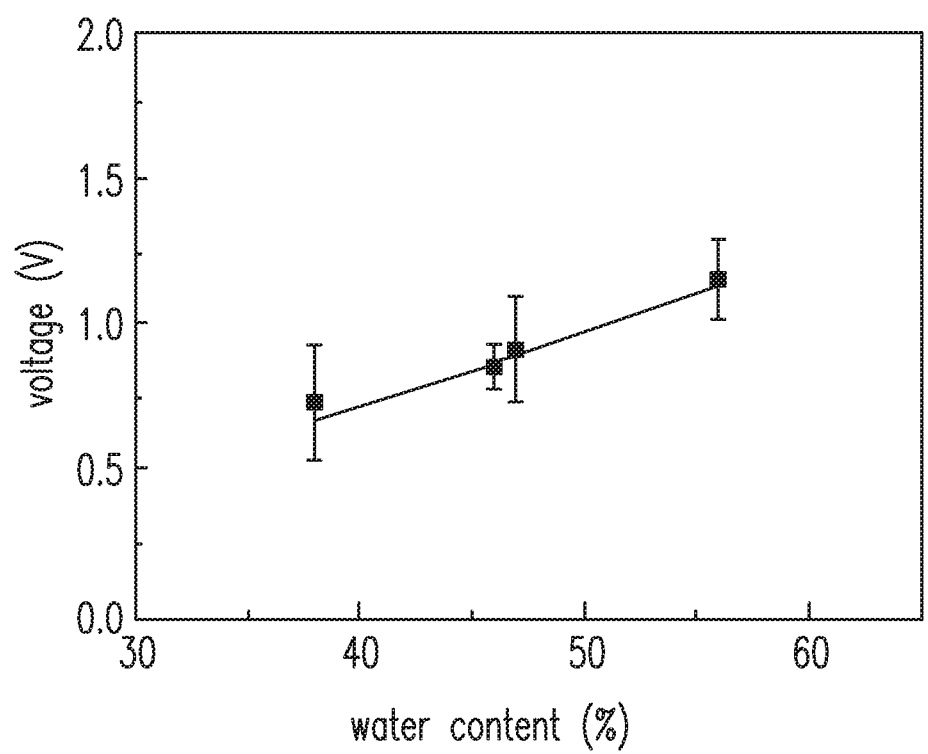
FIG. 2 is a graph showing the water content-voltage relationship for an embodiment of the present invention.

Please refer to FIG. 2, which is a graph showing the water content-voltage relationship established by a plurality of standardized ophthalmic lenses having a plurality of standardized water contents for an embodiment of the present invention. Different data points in FIG. 2 represent standardized ophthalmic lenses made of different specific materials. The data points in FIG. 2 are measured through the following method (referring to the optical inspection system 100 in FIG. 1): (g1) placing a specific one of the plurality of standardized ophthalmic lenses in the irradiation path; (g2) emitting the incident light from the light source 10 and causing the incident light to pass through the specific one to generate transmitted light at the $T_0$ instant, and using the light detector 20 to measure the light intensity of the transmitted light at the $T_0$ instant; (g3) converting the light intensity into a voltage with the signal amplifier circuit 30; (g4) performing steps (g1) to (g3) for each of the plurality of standardized ophthalmic lenses other than the specific one; and (g5) subtracting the first voltage from the voltage for each of the plurality of standardized ophthalmic lenses to obtain a plurality of standardized initial attenuation voltages. Each of the plurality of standardized ophthalmic lenses can be measured many times to obtain an average value and a standard deviation, as shown by the data points in FIG. 2 in the direction along the "voltage" axis. The horizontal axis is "water content." The plurality of standardized initial attenuation voltages is plotted as a function of the plurality of standardized water contents in FIG. 2 and a polynomial fit is made. It is seen from FIG. 2 that the water content (WC) is linearly related to the voltage $V_{i\kappa}$. The water content-voltage relationship $V_{i\theta}=0.0256 \times WC-0.30956$ is obtained from the polynomial fit. Then the initial attenuation voltage of the test ophthalmic lens is substituted into $V_{i\kappa}$ in the above relationship to calculate the water content of the test ophthalmic lens.

It is known from the above description that the measurement method to obtain the water content-voltage relationship is the same as that of inspecting the test ophthalmic lens, and the light intensity of the transmitted light is immediately measured at the same $T_0$ instant. The water content of the test ophthalmic lens obtained in this way is equivalent to the water content inspected by the standardized inspecting method.

In an example, the test ophthalmic lens and the plurality of standardized ophthalmic lenses in the above inspecting method are all contact lenses.

The method for inspecting the oxygen transmissibility of a test ophthalmic lens under a specific condition is the following: (a) emitting an incident light having a first light intensity and measuring the first light intensity; (b) converting the first light intensity into a first voltage; (c) placing the test ophthalmic lens in the irradiation path; (d) emitting the incident light to pass through the test ophthalmic lens to obtain transmitted light having a second light intensity $I_{2(0)}$ at a $T_0$ instant; (e) repetitively measuring at time points from $T_1$ to $T_n$ the transmitted light with a time interval of $\Delta t$ to obtain a plurality of subsequent second light intensities $I_{2(\Delta t)}, I_{2(2\Delta t)}, \ldots$ and $I_{2(n\Delta t)}$, where n is a positive integer; (f) converting the second light intensity and the plurality of subsequent second light intensities into a plurality of second voltages $V_{2(0)}, V_{2(\Delta t)}, V_{2(2\Delta t)}, \ldots$ and $V_{2(n\Delta t)}$; (g) obtaining a difference of the first voltage and each of the plurality of second voltages to obtain a plurality of attenuation voltages; (h) identifying a highest value in the plurality of attenuation voltages, wherein the highest value occurs at a specific time point $T_s$ being one selected from the group consisting of $T_0$, $T_1$ to $T_n$; (i) finding from the plurality of attenuation voltages a specific attenuation voltage after a preset specific time period from $T_s$; (j) calculating a difference of the specific attenuation voltage and the highest value to obtain a difference voltage; and (k) introducing the difference voltage into an oxygen transmissibility-voltage relationship established by a plurality of standardized ophthalmic lenses to obtain the oxygen transmissibility of the test ophthalmic lens. In an embodiment, obtaining a difference of the first voltage and each of the plurality of second voltages means subtracting the first voltage from each of the plurality of second voltages. In an embodiment, calculating a difference of the specific attenuation voltage and the highest value means subtracting the specific attenuation voltage from the highest value. In an example, the specific condition of the test ophthalmic lens is similarly a power of −3.00 D; the oxygen transmissibility of the test ophthalmic lens equivalent to the oxygen transmissibility inspected by the standardized inspecting method can be obtained by the method for any test ophthalmic lens having a power of −3.00 D.

Figure 3:
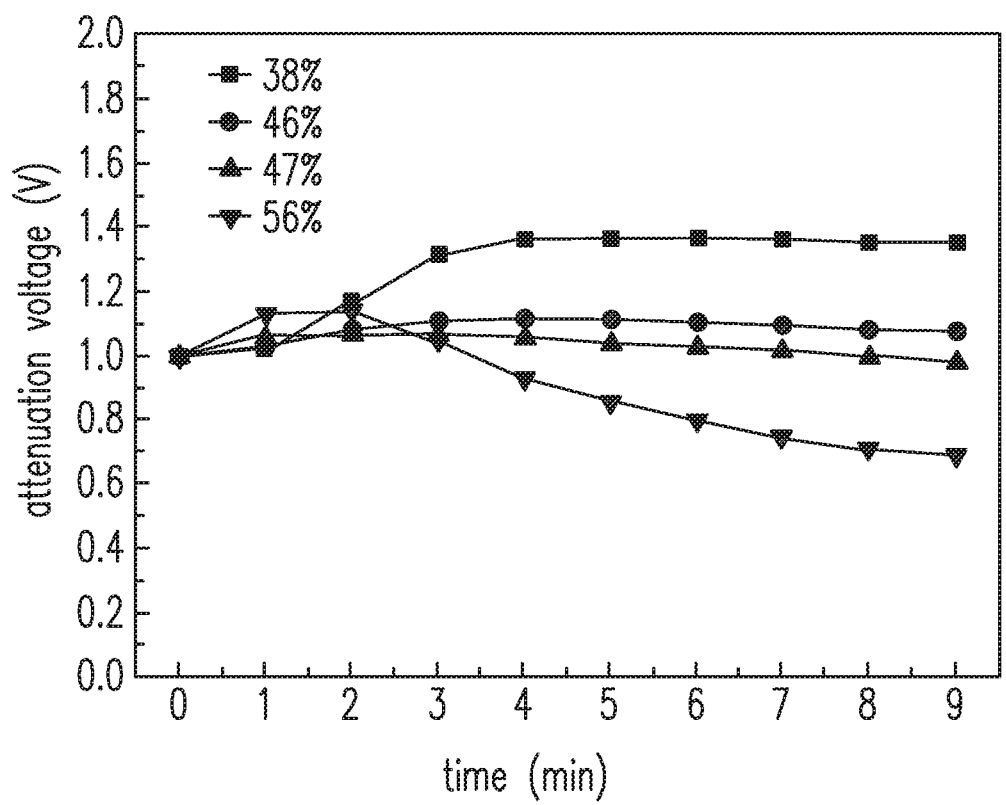
FIG. 3 is a graph showing attenuation voltage as a function of time for an embodiment of the present invention.

About the above-mentioned preset specific time period from $T_s$, please refer to FIG. 3, which is a graph showing attenuation voltage as a function of time for an embodiment of the present invention. In FIG. 3 $\Delta t=1$ min. In other words, FIG. 3 shows the attenuation voltages inspected by the optical inspection system at $T_0=0$ min, $T_1=1$ min, ... to $T_9=9$ min. The four symbols in FIG. 3 represent respectively standardized ophthalmic lenses made of four different specific materials. The standardized water contents of the respective standardized ophthalmic lenses are indicated in FIG. 3. It is seen from FIG. 3 that the attenuation voltage first rises to the highest value. If the time to reach the highest value is m$\Delta t$, then during the time period from $T_0$ to m$\Delta t$, the water content changes with time and affects the light intensity of transmitted light. Then the oxygen transmissibility affects the light intensity of transmitted light after m$\Delta t$. It is seen from FIG. 3 that the attenuation voltage gradually stops changing 3 min after mΔt. Thus, in the embodiment shown by FIG. 3, the preset specific time period is 3 min. The preset specific time period may be different for ophthalmic lenses made of materials of different specific types. In the present specification, the preset specific time period is equal to or smaller than 7 min. For example, 3 min, 4 min, 5 min, 6 min, 7 min or any time period between the adjacent integral minutes.

Figure 4:
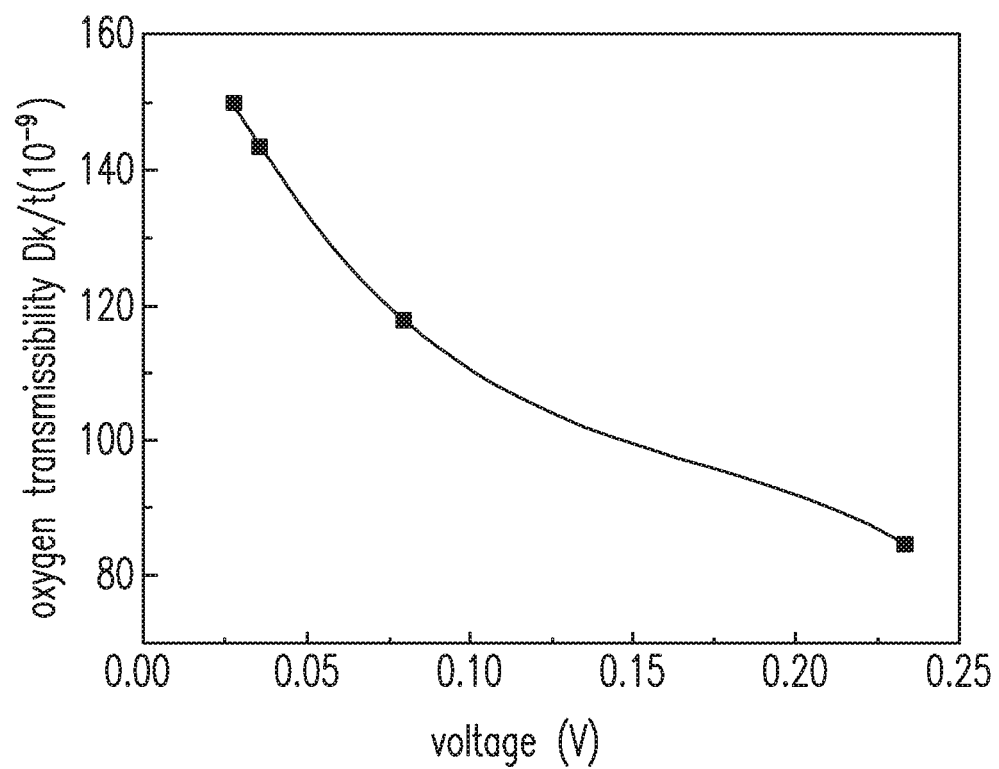
FIG. 4 is a graph showing the oxygen transmissibility-voltage relationship for an embodiment of the present invention.

About the above-mentioned oxygen transmissibility-voltage relationship established by a plurality of standardized ophthalmic lenses, please refer to FIG. 4, which is a graph showing the oxygen transmissibility-voltage relationship for an embodiment of the present invention. Different data points in FIG. 4 represent standardized ophthalmic lenses made of different specific materials. The data points in FIG. 4 are measured through the following method: (k1) placing a specific one of the plurality of standardized ophthalmic lenses in the irradiation path, wherein each of the plurality of standardized ophthalmic lenses has a standardized oxygen transmissibility; (k2) emitting the incident light to pass through the specific standardized ophthalmic lens to obtain a standardized transmitted light at the $T_0$ instant, and measuring a light intensity of the standardized transmitted light at the $T_0$ instant; (k3) repetitively measuring at the time points $T_1$ to $T_n$ the standardized transmitted light with a time interval of $\Delta t$ to obtain a plurality of subsequent light intensities; (k4) converting the light intensity and the plurality of subsequent light intensities into a plurality of voltages; (k5) subtracting the first voltage from each of the plurality of voltages to obtain a plurality of standardized attenuation voltages; (k6) identifying a standardized highest value in the plurality of standardized attenuation voltages, wherein the standardized highest value occurs at a specific time point being one selecting from the group consisting of $T_0$, $T_1$ to $T_n$; (k7) finding from the plurality of standardized attenuation voltages a specific standardized attenuation voltage after the preset specific time period from $T_s$; (k8) subtracting the specific standardized attenuation voltage from the standardized highest value to obtain a standardized difference voltage; and (k9) performing steps (k1) to (k8) for each of the plurality of standardized ophthalmic lenses other than the specific standardized ophthalmic lens. The standardized oxygen transmissibility is plotted as a function of the standardized difference voltage in FIG. 4, where the vertical axis is Dk/t, whose magnitude is $10^{-9}$ and the unit is $(cm^2 [O_2] \times cm)/(cm^2 \times Sec \times mm\ Hg)$, the horizontal axis is V, and a polynomial fit is made. The method for measuring the data points in FIG. 4 further includes: (k10) establishing the oxygen transmissibility-voltage relationship based on each the standardized oxygen transmissibility and each the standardized difference voltage of each the corresponding standardized ophthalmic lens. The oxygen transmissibility-voltage relationship $Dk/t=175.44-1101.39 \times V+5626.76 \times V^2-10996.39 \times V^3$ is obtained from the polynomial fit. Then the difference voltage of the test ophthalmic lens is substituted into V in the above relationship to calculate the oxygen transmissibility of the test ophthalmic lens.

The measurement method to obtain the oxygen transmissibility-voltage relationship is basically the same as that of inspecting the test ophthalmic lens. The oxygen transmissibility of the test ophthalmic lens obtained in this way is equivalent to the oxygen transmissibility inspected by the standardized inspecting method.

Because the difference voltage has to be calculated when the oxygen transmissibility is inspected and the two first voltages are canceled out when the attenuation voltage is subtracted from the highest value, and thus the measurement of the first voltage and related steps can be omitted.

If the test ophthalmic lens is not a contact lens having a power of −3.00 D, e.g. the oxygen transmissibility of a contact lens made of a specific material and having a power of −8.00 D is going to be inspected, then the contact lens made of the specific material and having a power of −3.00 D is first inspected using the above method. The contact lens made of the specific material and having a power of −3.00 D is then taken as a standardized ophthalmic lens to measure the standardized initial attenuation voltage. Next, the following method is utilized to obtain the oxygen transmissibility of the contact lens having a power of −8.00 D.

The method for inspecting the oxygen transmissibility of a test ophthalmic lens, wherein the test ophthalmic lens is made of the specific material, a standardized ophthalmic lens made of the specific material has a standardized initial attenuation voltage, and the standardized ophthalmic lens under a specific condition has a standardized oxygen transmissibility, the method includes: (a) emitting the incident light having the first light intensity and measuring the first light intensity; (b) placing the test ophthalmic lens in the irradiation path; (c) passing the incident light through the test ophthalmic lens to generate a transmitted light having a second light intensity at the $T_0$ instant; (d) converting the first and the second light intensities into a first and a second voltages respectively, wherein the difference between the first and the second voltages is an initial attenuation voltage; (e) dividing the initial attenuation voltage by the standardized initial attenuation voltage to obtain a constant of proportionality; and (f) multiplying the standardized oxygen transmissibility by the constant of proportionality to obtain the oxygen transmissibility of the test ophthalmic lens.

In an embodiment, the test ophthalmic lens and the standardized ophthalmic lens are both contact lenses having a power of −3.00 D. The standardized initial attenuation voltage is denoted as $V_{iK}$ (@−3.00 D), the initial attenuation voltage of the test ophthalmic lens is denoted as $V_{iK}$ (@−xD), and the constant of proportionality is denoted as $R'=V_{iK}$ (@−xD)$/V_{iK}$ (A−3.00 D). The oxygen transmissibility of the standardized ophthalmic lens is denoted as Dk/t (@−3.00 D), and the oxygen transmissibility of the test ophthalmic lens is Dk/t (@−xD)=Dk/t (@−3.00 D)×R'.

Embodiments

1. A method for inspecting a water content of a test ophthalmic lens, including: (a) emitting an incident light having an irradiation path and a first light intensity; (b) converting the first light intensity into a first voltage; (c) placing the test ophthalmic lens in the irradiation path; (d) emitting the incident light to pass through the test ophthalmic lens to obtain a transmitted light having a second light intensity at a $T_0$ instant; (e) converting the second light intensity into a second voltage; (f) calculating a difference between the first voltage and the second voltage to obtain an initial attenuation voltage; and (g) obtaining the water content of the test ophthalmic lens based on the initial attenuation voltage.

2. The method according to Embodiment 1, wherein the incident light is emitted by a green light-emitting diode (LED).

3. The method according to Embodiment 1 or 2, wherein an optical inspection system is provided and includes a signal amplifier circuit converting the first light intensity into the first voltage decreasing with an increase in the first light intensity.

4. The method according to any one of Embodiments 1 to 3, wherein the initial attenuation voltage is introduced into a water content-voltage relationship established by a plurality of standardized ophthalmic lenses to obtain the water content of the test ophthalmic lens.

5. The method according to any one of Embodiments 1 to 4, wherein the test ophthalmic lens and the plurality of standardized ophthalmic lenses are all contact lenses.

6. The method according to any one of Embodiments 1 to 5, wherein an optical inspection system is provided and includes a light source and a light detector, and the water content-voltage relationship is obtained through the following steps: (g1) placing a specific one of the plurality of standardized ophthalmic lenses in the irradiation path, wherein each of the plurality of standardized ophthalmic lenses has a standardized water content; (g2) emitting the incident light from the light source and causing the incident light to pass through the specific one to generate a transmitted light at the $T_0$ instant, and using the light detector to measure a light intensity of the transmitted light at the $T_0$ instant; (g3) converting the light intensity into a voltage; (g4) performing steps (g1) to (g3) for each of the plurality of standardized ophthalmic lenses other than the specific one; (g5) subtracting the first voltage from the voltage for each of the plurality of standardized ophthalmic lenses to obtain a plurality of standardized initial attenuation voltages; and (g6) establishing the water content-voltage relationship based on each the standardized water content and each the standardized initial attenuation voltage of each the corresponding standardized ophthalmic lens.

7. A method for inspecting an oxygen transmissibility of a test ophthalmic lens, including: (a) emitting an incident light having an irradiation path and a first light intensity; (b) converting the first light intensity into a first voltage; (c) placing the test ophthalmic lens in the irradiation path; (d) emitting the incident light to pass through the test ophthalmic lens to obtain a transmitted light having a second light intensity $I_{2(0)}$ at a $T_0$ instant; (e) repetitively measuring at time points from $T_1$ to $T_n$ the transmitted light with a time interval of $\Delta t$ to obtain a plurality of subsequent second light intensities $I_{2(\Delta t)}$, $I_{2(2\Delta t)}$, ... and $I_{2(n\Delta t)}$, where n is a positive integer; (f) converting the second light intensity and the plurality of subsequent second light intensities into a plurality of second voltages $V_{2(0)}$, $V_{2(\Delta t)}$, $V_{2(2\Delta t)}$, ... and $V_{2(n\Delta t)}$; (g) obtaining a difference of the first voltage and each of the plurality of second voltages to obtain a plurality of attenuation voltages; (h) identifying a highest value in the plurality of attenuation voltages, wherein the highest value occurs at a specific time point $T_s$ being one selected from the group consisting of $T_0$, $T_1$ to $T_n$; (i) finding from the plurality of attenuation voltages a specific attenuation voltage after a preset specific time period less than 7 minutes from $T_s$; (j) calculating a difference of the specific attenuation voltage and the highest value to obtain a difference voltage; and (k) introducing the difference voltage into an oxygen transmissibility-voltage relationship established by a plurality of standardized ophthalmic lenses to obtain the oxygen transmissibility of the test ophthalmic lens.

8. The method according to Embodiment 7, wherein the oxygen transmissibility-voltage relationship is obtained through the following steps: (k1) placing a specific one of the plurality of standardized ophthalmic lenses in the irradiation path, wherein each of the plurality of standardized ophthalmic lenses has a standardized oxygen transmissibility; (k2) emitting the incident light to pass through the specific standardized ophthalmic lens to obtain a standardized transmitted light at the $T_0$ instant, and measuring a light intensity of the standardized transmitted light at the $T_0$ instant; (k3) repetitively measuring at the time points $T_1$ to $T_n$ the standardized transmitted light with a time interval of $\Delta t$ to obtain a plurality of subsequent light intensities; (k4) converting the light intensity and the plurality of subsequent light intensities into a plurality of voltages; (k5) subtracting the first voltage from each of the plurality of voltages to obtain a plurality of standardized attenuation voltages; (k6) identifying a standardized highest value in the plurality of standardized attenuation voltages, wherein the standardized highest value occurs at a specific time point being one selecting from the group consisting of $T_0$, $T_1$ to $T_n$; (k7) finding from the plurality of standardized attenuation voltages a specific standardized attenuation voltage after the preset specific time period from $T_s$; (k8) subtracting the specific standardized attenuation voltage from the standardized highest value to obtain a standardized difference voltage; (k9) performing steps (k1) to (k8) for each of the plurality of standardized ophthalmic lenses other than the specific standardized ophthalmic lens; and (k10) establishing the oxygen transmissibility-voltage relationship based on each the standardized oxygen transmissibility and each the standardized difference voltage of each the corresponding standardized ophthalmic lens.

9. A method for inspecting an oxygen transmissibility of a test ophthalmic lens, including: (a) placing the test ophthalmic lens in an irradiation path of an incident light; (b) emitting the incident light to pass through the test ophthalmic lens to obtain a transmitted light having a light intensity $I_0$ at a $T_0$ instant; (c) repetitively measuring the transmitted light at time points from $T_1$ to $T_n$ with a time interval of $\Delta t$ to obtain a plurality of subsequent light intensities $I_{\Delta t}$, $I_{2\Delta t}$, ... and $I_{n\Delta t}$, where n is a positive integer; (d) converting the light intensity and the plurality of subsequent light intensities into a plurality of voltages $V_0$, $V_{\Delta t}$, $V_{2\Delta t}$, ... and $V_{n\Delta t}$; (e) identifying a highest value in the plurality of voltages, wherein the highest value occurs at a specific time point $T_s$ being one selected from the group consisting of $T_0$, $T_1$ to $T_n$; (f) finding from the plurality of voltages a specific voltage after a preset specific time period less than 7 minutes from $T_s$; (g) calculating a difference of the specific voltage and the highest value to obtain a difference voltage; and (h) obtaining the oxygen transmissibility of the test ophthalmic lens based on the difference voltage.

10. The method according to Embodiment 9, wherein the difference voltage is introduced into an oxygen transmissibility-voltage relationship established by a plurality of standardized ophthalmic lenses to obtain the oxygen transmissibility of the test ophthalmic lens.

11. A method for inspecting an oxygen transmissibility of a test ophthalmic lens, wherein the test ophthalmic lens is made of a specific material, a standardized ophthalmic lens made of the specific material has a standardized initial attenuation voltage, and the standardized ophthalmic lens under a specific condition has a standardized oxygen transmissibility, the method including: (a) emitting an incident light having an irradiation path, wherein the incident light has a first light intensity; (b) placing the test ophthalmic lens in the irradiation path; (c) passing the incident light through the test ophthalmic lens to generate a transmitted light having a second light intensity at a $T_0$ instant; (d) converting the first and the second light intensities into a first and a second voltages respectively, wherein the difference between the first and the second voltages is an initial attenuation voltage; (e) dividing the initial attenuation voltage by the standardized initial attenuation voltage to obtain a constant of proportionality; and (f) multiplying the standardized oxygen transmissibility by the constant of proportionality to obtain the oxygen transmissibility of the test ophthalmic lens.

12. The method according to Embodiment 11, wherein the standardized attenuation voltage is obtained through the following steps: (g1) placing the standardized ophthalmic lens in the irradiation path; (g2) when the incident light passes through the standardized ophthalmic lens to obtain a transmitted light at the $T_0$ instant, measuring a light intensity of the transmitted light at the $T_0$ instant; (g3) converting the light intensity into a third voltage; and (g4) subtracting the first voltage from the third voltage to obtain the standardized attenuation voltage.

13. An optical inspecting system for inspecting an ophthalmic lens, including: a light source emitting an incident light having an irradiation path; a photo detector inspecting a first light intensity of the incident light and inspecting a second light intensity of a transmitted light obtained when the incident light passes through the ophthalmic lens at an instant being one selected from a group consisting of $T_0$, $T_1 \ldots T_{n-1}$ and $T_n$ where n is a positive integer; a signal amplifier circuit converting the first and the second light intensities into a first and a second voltages respectively; and a computer processing unit calculating a water content and an oxygen transmissibility of the ophthalmic lens according to the first and the second voltages, wherein the water content is measured at the $T_0$ instant.

14. The optical testing system according to Embodiment 13, wherein the optical testing system further comprises a controller electrically connected to the computer processing unit and adjusting the first light intensity of the incident light.

15. The optical testing system according to Embodiment 13 or 14, wherein the first voltage decreases as the first light intensity increases.

16. The optical testing system according to any one of Embodiments 13 to 15, wherein the ophthalmic lens is a contact lens.

17. The optical testing system according to any one of Embodiments 13 to 16, wherein the light source is a green light-emitting diode (LED).

18. The optical testing system according to any one of Embodiments 13 to 17, wherein the green light-emitting diode (LED) emits a green light having a 520 nm wavelength and is triggered by a 1 mA current.

19. The optical testing system according to any one of Embodiments 13 to 18, wherein the optical testing system further comprises a voltage measurement unit configured between the signal amplifier circuit and the computer processing unit for measuring values of the first and the second voltages and then sending the values of the first and the second voltages to the computer processing unit to calculate the water content and the oxygen transmissibility.

20. The optical testing system according to any one of Embodiments 13 to 19, wherein the voltage measurement unit is an oscilloscope.

What is claimed is:

1. A method for inspecting a water content of a test ophthalmic lens, comprising:
   (a) emitting an incident light having an irradiation path and a first light intensity;
   (b) converting the first light intensity into a first voltage;
   (c) placing the test ophthalmic lens in the irradiation path;
   (d) emitting the incident light to pass through the test ophthalmic lens to obtain a transmitted light having a second light intensity at a $T_0$ instant;
   (e) converting the second light intensity into a second voltage;
   (f) calculating a difference between the first voltage and the second voltage to obtain an initial attenuation voltage; and
   (g) obtaining the water content of the test ophthalmic lens based on the initial attenuation voltage.

2. The method as claimed in claim 1, wherein the incident light is emitted by a green light-emitting diode (LED).

3. The method as claimed in claim 1, wherein an optical inspection system is provided and includes a signal amplifier circuit converting the first light intensity into the first voltage decreasing with an increase of the first light intensity.

4. The method as claimed in claim 1, wherein the initial attenuation voltage is introduced into a water content-voltage relationship established by a plurality of standardized ophthalmic lenses to obtain the water content of the test ophthalmic lens.

5. The method as claimed in claim 4, wherein the test ophthalmic lens and the plurality of standardized ophthalmic lenses are all contact lenses.

6. The method as claimed in claim 4, wherein an optical inspection system is provided and includes a light source and a light detector, and the water content-voltage relationship is obtained through the following steps:
   (g1) placing a specific one of the plurality of standardized ophthalmic lenses in the irradiation path, wherein each of the plurality of standardized ophthalmic lenses has a standardized water content;
   (g2) emitting the incident light from the light source and causing the incident light to pass through the specific one to generate a transmitted light at the $T_0$ instant, and using the light detector to measure a light intensity of the transmitted light at the $T_0$ instant;
   (g3) converting the light intensity into a voltage;
   (g4) performing steps (g1) to (g3) for each of the plurality of standardized ophthalmic lenses other than the specific one;
   (g5) subtracting the first voltage from the voltage for each of the plurality of standardized ophthalmic lenses to obtain a plurality of standardized initial attenuation voltages; and
   (g6) establishing the water content-voltage relationship based on each the standardized water content and each the standardized initial attenuation voltage of each the corresponding standardized ophthalmic lens.

7. A method for inspecting an oxygen transmissibility of a test ophthalmic lens, comprising:
   (a) emitting an incident light having an irradiation path and a first light intensity;
   (b) converting the first light intensity into a first voltage;
   (c) placing the test ophthalmic lens in the irradiation path;
   (d) emitting the incident light to pass through the test ophthalmic lens to obtain a transmitted light having a second light intensity $I_{2(0)}$ at a $T_0$ instant;
   (e) repetitively measuring at time points from $T_1$ to $T_n$ the transmitted light with a time interval of $\Delta t$ to obtain a plurality of subsequent second light intensities $I_{2(\Delta t)}$, $I_{2(2\Delta t)}$, ... and $I_{2(n\Delta t)}$, where n is a positive integer;
   (f) converting the second light intensity and the plurality of subsequent second light intensities into a plurality of second voltages $V_{2(0)}$, $V_{2(\Delta t)}$, $V_{2(2\Delta t)}$, ... and $V_{2(n\Delta t)}$;
   (g) obtaining a difference of the first voltage and each of the plurality of second voltages to obtain a plurality of attenuation voltages;

(h) identifying a highest value in the plurality of attenuation voltages, wherein the highest value occurs at a specific time point $T_s$ being one selected from the group consisting of $T_0$, $T_1$ to $T_n$;
(i) finding from the plurality of attenuation voltages a specific attenuation voltage after a preset specific time period less than 7 minutes from $T_s$;
(j) calculating a difference of the specific attenuation voltage and the highest value to obtain a difference voltage; and
(k) introducing the difference voltage into an oxygen transmissibility-voltage relationship established by a plurality of standardized ophthalmic lenses to obtain the oxygen transmissibility of the test ophthalmic lens.

8. The method as claimed in claim 7, wherein the oxygen transmissibility-voltage relationship is obtained through the following steps:
(k1) placing a specific one of the plurality of standardized ophthalmic lenses in the irradiation path, wherein each of the plurality of standardized ophthalmic lenses has a standardized oxygen transmissibility;
(k2) emitting the incident light to pass through the specific standardized ophthalmic lens to obtain a standardized transmitted light at the $T_0$ instant, and measuring a light intensity of the standardized transmitted light at the $T_0$ instant;
(k3) repetitively measuring at the time points $T_1$ to $T_n$ the standardized transmitted light with a time interval of $\Delta t$ to obtain a plurality of subsequent light intensities;
(k4) converting the light intensity and the plurality of subsequent light intensities into a plurality of voltages;
(k5) subtracting the first voltage from each of the plurality of voltages to obtain a plurality of standardized attenuation voltages;
(k6) identifying a standardized highest value in the plurality of standardized attenuation voltages, wherein the standardized highest value occurs at a specific time point being one selecting from the group consisting of $T_0$, $T_1$ to $T_n$;
(k7) finding from the plurality of standardized attenuation voltages a specific standardized attenuation voltage after the preset specific time period from $T_s$;
(k8) subtracting the specific standardized attenuation voltage from the standardized highest value to obtain a standardized difference voltage;
(k9) performing steps (k1) to (k8) for each of the plurality of standardized ophthalmic lenses other than the specific standardized ophthalmic lens; and
(k10) establishing the oxygen transmissibility-voltage relationship based on each the standardized oxygen transmissibility and each the standardized difference voltage of each the corresponding standardized ophthalmic lens.

9. A method for inspecting an oxygen transmissibility of a test ophthalmic lens, comprising:
(a) placing the test ophthalmic lens in an irradiation path of an incident light;
(b) emitting the incident light to pass through the test ophthalmic lens to obtain a transmitted light having a light intensity $I_0$ at a $T_0$ instant;
(c) repetitively measuring the transmitted light at time points from $T_1$ to $T_0$ with a time interval of $\Delta t$ to obtain a plurality of subsequent light intensities $I_{\Delta t}$, $I_{2\Delta t}$, . . . and $I_{n\Delta t}$, where n is a positive integer;
(d) converting the light intensity and the plurality of subsequent light intensities into a plurality of voltages $V_0$, $V_{\Delta t}$, $V_{2\Delta t}$, . . . and $V_{n\Delta t}$;
(e) identifying a highest value in the plurality of voltages, wherein the highest value occurs at a specific time point $T_s$ being one selected from the group consisting of $T_0$, $T_1$ to $T_n$;
(f) finding from the plurality of voltages a specific voltage after a preset specific time period less than 7 minutes from $T_s$;
(g) calculating a difference of the specific voltage and the highest value to obtain a difference voltage; and
(h) obtaining the oxygen transmissibility of the test ophthalmic lens based on the difference voltage.

10. The method as claimed in claim 9, wherein the difference voltage is introduced into an oxygen transmissibility-voltage relationship established by a plurality of standardized ophthalmic lenses to obtain the oxygen transmissibility of the test ophthalmic lens.

11. A method for inspecting an oxygen transmissibility of a test ophthalmic lens, wherein the test ophthalmic lens is made of a specific material, a standardized ophthalmic lens made of the specific material has a standardized initial attenuation voltage, and the standardized ophthalmic lens under a specific condition has a standardized oxygen transmissibility, the method comprising:
(a) emitting an incident light having an irradiation path, wherein the incident light has a first light intensity;
(b) placing the test ophthalmic lens in the irradiation path;
(c) passing the incident light through the test ophthalmic lens to generate a transmitted light having a second light intensity at a $T_0$ instant;
(d) converting the first and the second light intensities into a first and a second voltages respectively, wherein the difference between the first and the second voltages is an initial attenuation voltage;
(e) dividing the initial attenuation voltage by the standardized initial attenuation voltage to obtain a constant of proportionality; and
(f) multiplying the standardized oxygen transmissibility by the constant of proportionality to obtain the oxygen transmissibility of the test ophthalmic lens.

12. The method as claimed in claim 11, wherein the standardized attenuation voltage is obtained through the following steps:
(g1) placing the standardized ophthalmic lens in the irradiation path;
(g2) when the incident light passes through the standardized ophthalmic lens to obtain a transmitted light at the $T_0$ instant, measuring a light intensity of the transmitted light at the $T_0$ instant;
(g3) converting the light intensity into a third voltage; and
(g4) subtracting the first voltage from the third voltage to obtain the standardized attenuation voltage.

13. An optical inspecting system for inspecting an ophthalmic lens, comprising:
a light source emitting an incident light having an irradiation path;
a photo detector inspecting a first light intensity of the incident light and inspecting a second light intensity of a transmitted light obtained when the incident light passes through the ophthalmic lens at an instant being one selected from a group consisting of $T_0$, $T_1$ . . . $T_{n-1}$ and $T_n$ where n is a positive integer;
a signal amplifier circuit converting the first and the second light intensities into a first and a second voltages respectively; and a computer processing unit calculating a water content and an oxygen transmissibility of the ophthalmic lens according to the first and the second voltages, wherein the water content is measured at the $T_0$ instant.

14. The optical testing system as claimed in claim 13, wherein the optical testing system further comprises a controller electrically connected to the computer processing unit and adjusting the first light intensity of the incident light.

15. The optical testing system as claimed in claim 13, wherein the first voltage decreases as the first light intensity increases.

16. The optical testing system as claimed in claim 13, wherein the ophthalmic lens is a contact lens.

17. The optical testing system as claimed in claim 13, wherein the light source is a green light-emitting diode (LED).

18. The optical testing system as claimed in claim 17, wherein the green light-emitting diode (LED) emits a green light having a 520 nm wavelength and is triggered by a 1 mA current.

19. The optical testing system as claimed in claim 13, wherein the optical testing system further comprises a voltage measurement unit configured between the signal amplifier circuit and the computer processing unit for measuring values of the first and the second voltages and then sending the values of the first and the second voltages to the computer processing unit to calculate the water content and the oxygen transmissibility.

20. The optical testing system as claimed in claim 19, wherein the voltage measurement unit is an oscilloscope.

* * * * *